US006942864B2

(12) United States Patent
Spibey

(10) Patent No.: US 6,942,864 B2
(45) Date of Patent: Sep. 13, 2005

(54) LEPORIPOX-BASED VECTOR VACCINES

(75) Inventor: Norman Spibey, Cambs (GB)

(73) Assignee: Akzo Nobel N.V., Arnhem (NL)

(*) Notice: Subject to any disclaimer, the term of this patent is extended or adjusted under 35 U.S.C. 154(b) by 0 days.

(21) Appl. No.: 10/471,300

(22) PCT Filed: Mar. 7, 2002

(86) PCT No.: PCT/EP02/02858

§ 371 (c)(1),
(2), (4) Date: Sep. 8, 2003

(87) PCT Pub. No.: WO02/072852

PCT Pub. Date: Sep. 19, 2002

(65) Prior Publication Data

US 2004/0137599 A1 Jul. 15, 2004

(51) Int. Cl.$^7$ .................... A61K 39/275; A61K 39/295; C12N 7/01
(52) U.S. Cl. ................ 424/199.1; 424/232.1; 435/320.1; 435/235.1
(58) Field of Search .......................... 424/199.1, 232.1; 435/320.1, 235.1

(56) References Cited

U.S. PATENT DOCUMENTS

| 5,174,993 | A | | 12/1992 | Paoletti | |
|---|---|---|---|---|---|
| 5,505,941 | A | | 4/1996 | Paoletti | |
| 5,942,235 | A | | 8/1999 | Paoletti | |
| 6,001,349 | A | * | 12/1999 | Panicali et al. | 424/93.2 |
| 6,127,172 | A | * | 10/2000 | Moyer et al. | 435/320.1 |
| 6,294,176 | B1 | | 9/2001 | Cochran et al. | |
| 6,338,962 | B1 | * | 1/2002 | Boyce | 435/320.1 |
| 6,340,462 | B1 | | 1/2002 | Paoletti | |

FOREIGN PATENT DOCUMENTS

| EP | 0 652 287 A3 | | 5/1995 | |
|---|---|---|---|---|
| EP | 0 652 287 A2 | | 5/1995 | |
| EP | 0 972 840 | | 1/2000 | |
| EP | 0972840 A2 | * | 1/2000 | C12N/15/86 |
| FR | 2 736 358 | | 1/1997 | |
| WO | WO 89/03429 | * | 4/1989 | C12P/12/00 |
| WO | WO 93/01284 | | 1/1993 | |
| WO | WO 99/61069 | | 12/1999 | |

OTHER PUBLICATIONS

Tartaglia et al (Journal of Virology 67:2370–2375, 1993).*
Pastoret, P.P. et al, Dev. Biol. Stand. Basel, Karger, V84 p183–193, (1995): Target and Non–Target Effects of a Recombinant Vaccinia–Rabies Virus Developed for Fox . . .
Paoletti, E. et al, Dev. Biol. Stand., Basel, Karger, V82 p65–69, (1994): Safe and Effective Poxvirus Vectors–NY-VAC and ALVAC.
Perkus, M.E., et al, Ann.N.Y. Acad. Sci., V75, p222–233 (May 1995): Live Attenuated Vaccinia and Other Poxviruses as Delivery Systems: Public Health Issues.
Messud–Petit, F., Virologie, V4, N6, p453–462, (Nov.–Dec. 2000) "Le virus myxomateux: de l'agent pathogene au vecteur vaccinal".
Jackson, R.J., et al, J. of General Virology V73, p3241–3245 (1992): "A myxoma virus intergenic transient dominant selection vector".
Holland, M.K., et al, Reprod. Fertil. Dev., 6(5), p631–642, (1994): Virus–vectored Immunocontraception for Control of Wild Rabbits: Identification of Target Antigens . . .
Jackson, R. J., et al, J. Gen. Virol., V77, p1569–1575, (1996): Construction of recombinant myxoma viruses expressing foreign genes from different intergenic sites without . . .
Tyndale–Biscoe, C.H., Reprod. Fertil. Deve. V6, p281–287 (1994) Virus–vectored Immunocontraception of Feral Mammals.
Robinson, A.J., et al, 1995 Joint Conference AAZV/WDA/AAWV: Recombinant myxoma viruses containing reproductive tract antigens: can they be used to control wild rabbit in . . .
Hu, Liangbiao et al (Cornell Universtiy, Ph.D., DAI V55(11), SECB, p4746) (Jan. 1995): Development of raccoon poxvirus–vectored feline recombinant vaccines.
Fischer, L. et al., Vaccine, V15 N1, p90–96 (1997): A recombiant canarypox virus protects rabbits against a lethal rabbit hemorrhagic disease virus (RHDV) challenge.
Kerr, P. et al., Vaccine, V13, N17, p1722–1726 (1995): Myxoma virus as a vaccine vector for rabbits: antibody levels to influenza virus haemagglutinin presented by a . . .
Opgenorth, A., et al., J. Virology, V66, N8, p 4720–4731 (Aug. 1992): Deletion Analysis of Two Tandemly Arranged Virulence Genes in Myxoma Virus, M11L and Myxoma Growth . . .

(Continued)

Primary Examiner—Mary E. Mosher
(74) Attorney, Agent, or Firm—Mark W. Milstead

(57) ABSTRACT

The present invention is directed to the use of a live, recombinant leporipox virus comprising exogenous DNA, which is operably linked to at least one expression control element and which is incorporated in a non-essential region of the virus genome, in the manufacture of a vector vaccine for the treatment and/or prophylaxis of infectious diseases in non-lepori species. The invention furthermore relates to a live, recombinant leporipox virus comprising exogenous DNA operably linked to at least one expression control element and incorporated in a non-essential region of the virus genome characterized in that said exogenous DNA encodes at least one antigen of a non-lepori pathogen. Due to its restricted host-range the recombinant leporipox virus is non-pathogenic in non-susceptible hosts such as non-lepori vertebrates. Vaccination with said recombinant leporipox virus induced an antigen or immunogenic response in the vaccinated non-lepori host even though productive replication of the virus was not observed in the host.

13 Claims, 3 Drawing Sheets

OTHER PUBLICATIONS

Figure 1:
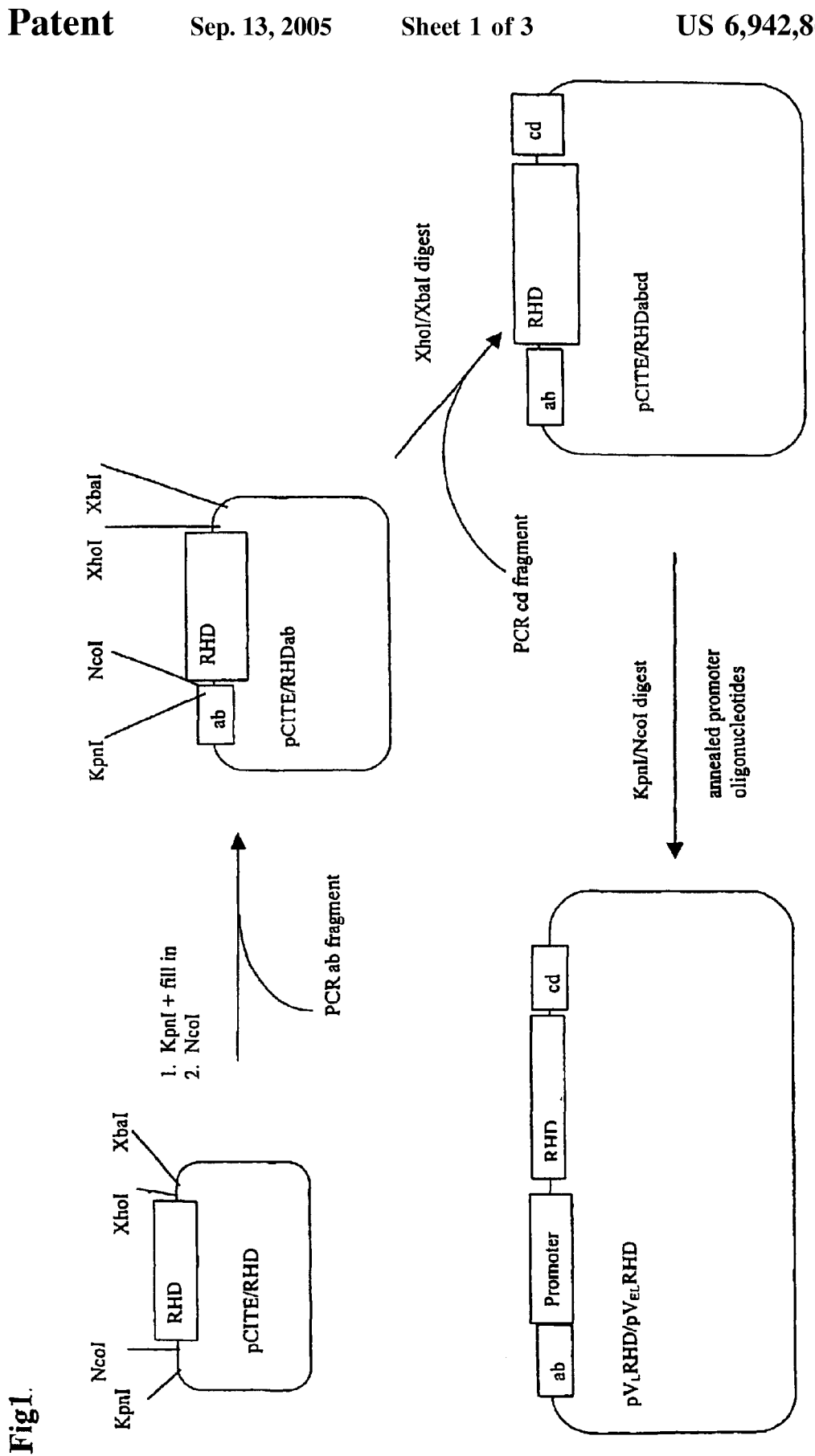
Figure 1:
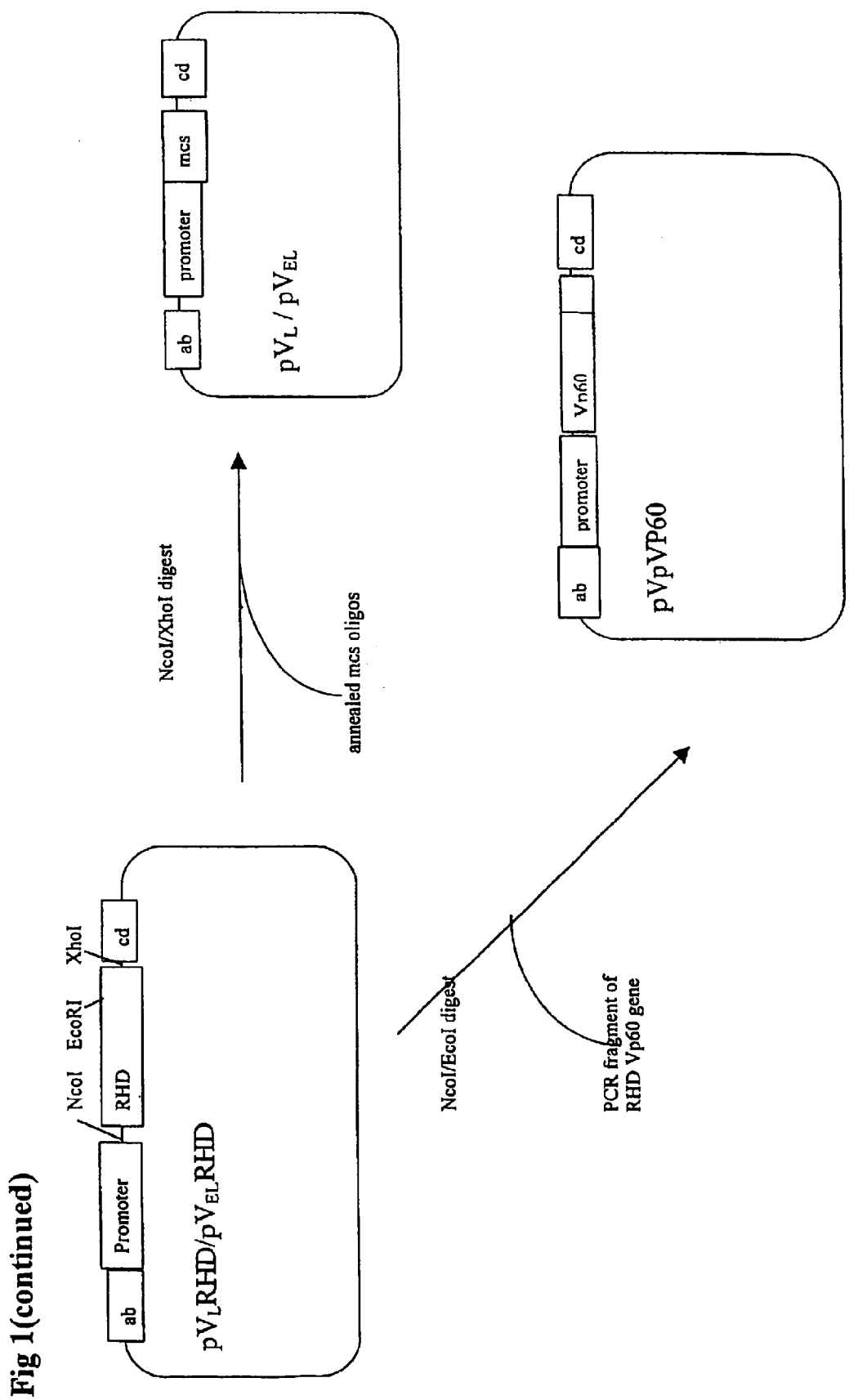

Hu, Liangbiao, et al., Vaccine, V15, N12/13, p1466–1472 (1997): Raccoon poxvirus live recombinant feline panleukopenia virus VP2 and rabies virus glycoprotein bivalent . . .

Taylor, J., et al., Vaccine, V15, N12/13, p539–549 (1995): Biological and immunogenic properties of a canarypox–rabies recombinant, ALVAC–RG (vCP65) in non–avian species.

Pincus, S., et al., Biologicals V23, p159–164 (Jun. 1995): Poxvirus–Based Vectors as Vaccine Candidates.

Bertagnoli, S., et al., Vaccine, V14, N6, p506–510 (1996): Protection of rabbits against rabbit viral haemorrhagic disease with a vaccinia–RHDV recombinant virus.

Paoletti, E., Proc. Natl. Acad. Sci. USA V93, p11349–11353 (Oct. 1996): Applications of pox virus vectors to vaccination: An update.

Rodriguez, D., et al., Proc. Natl. Acad. Sci. USA V86, p1287–1291 (Feb. 1989): Highly attenuated vaccina virus mutants for the generation of safe recombinant viruses.

Perkus, M., et al., J. of Virology, V63, N9, p3829–3836 (Sep. 1989): Cloning and Expression of Foreign Genes in Vaccinia Virus, Using a Host Range Selection System.

Welter, J. et al., Vaccine, V17 p308–318, (1999) Mucosal vaccination with recombinant poxvirus vaccines protects ferrets against symptomatic CDV infection.

Taylor, J. Prog.vet Microbiol. Immun. V4, p197–217 (1998): Pox viruses as eukaryotic cloning and expression vectors: future medical and veterinary vaccines.

Taylor, J. et al., Vaccine, V6 p 497–503 (Dec. 1998): Recombinant fowlpox virus inducing protective immunity in non–avaian species.

Taylor, J. et al., Vaccine, V 6 p466–468 (Dec. 1998): Fowlpox virus as a vector in non–avian species.

Dallo, S., et al., Virology, V173, p323–329 (1989): Humoral Immune Response Elicited by Highly Attenuated Variants of Variants Virus and by an Attenuated Recombinant . . .

Tartaglia J et al: "Protection of Cats Against Feline Leukemia Virus by Vaccination with a Canarypox Virus Recombinant, ALVAC–FL"; Journal of Virology, New York, US, US, vol. 67, No. 4, Apr. 1993; pp. 2370–2375.

Barcena J. et al: "Horizontal Transmission Protection Against Myxomatosis and Rabbit Hemorrhagic Disease by Using a Recombinant Myxoma Virus"; J. Virology, vol. 74, No. 3, Feb. 2000; pp. 1114–1123.

Paoletti Enzo: "Applications of Pox Virus Vectors to Vaccination: An Update"; Proceedings of the National Academy of Sciences of USA, US, National Academy of Science, Washington; vol. 93, No. 21; Oct. 1996.

* cited by examiner

Fig 2

| ab | P | RHDV VP60 | cd | pVL/VP60 pVEL/VP60

| ab | P | FCV VP60 | cd | pVL/FCV pVEL/FCV

| ab | P | CPV / Vp2 | cd | pVL/CPV pVEL/CPV

| ab | P | FeLV gp85 | cd | pVL/FeLV env pVEL/FeLV env

| ab | P | FPL Vp2 | cd | pVL/FPL pVEL/FPL

| ab | P | GFP | cd | pVL/GFP pVEL/GFP

LEPORIPOX-BASED VECTOR VACCINES

This application is the National Stage of International Application No. PCT/EP02/02858, filed Mar. 7, 2002.

The present invention relates to the use of a leporipox virus vector vaccine in non-susceptible host species and live, recombinant leporipox viruses.

Vector vaccines based on orthopox and avipox viruses and their potential as recombinant viral vectors in vaccination have been described. U.S. Pat. No. 5,759,841 describes a recombinant vaccinia virus which contain morbillivirus DNA coding for at least one glycoprotein, and a promoter for expression of the DNA, In a non-essential region of the vaccinia virus genome. The recombinant vaccinia virus can be used in vaccines for inducing an immune response to morbillivirus in dogs. The recombinant vaccinia vector virus however is permissive in a great number of different species including humans hence the described vaccinia vector virus has the potential risk of causing a runaway infection in the vaccinated host or of transmission from vaccinated to unvaccinated hosts.

WO 9527780 describes a recombinant avipox virus, which by virtue of its restricted host-range has attenuated virulence in a non-avian host The recombinant avipox viruses contain exogenous DNA in a non-essential region of the virus genome, whereby the exogenous DNA encodes at least one Canine Distemper virus (CDV) antigen, or measles virus (MV) M or N antigen. These viruses can be used to induce an antigenic or immunologic response in canines and other carnivores as well as in humans. The recombinant avipox vector viruses are restricted to their natural host and vaccination of non-avian species with said vector viruses results in expression of the exogenous antigen without productive replication of the virus. However the level of expression of the exogenous antigen remains low after vaccination with the avipox virus vector. Hence there is a need for improved expression levels of the exogenous antigen. Furthermore immunization with avipox virus vector does not always provide sufficient neutralizing antibodies against the exogenous antigen. Vaccination of cats with a canary pox-based FeLV vector vaccine did not lead to the production of neutralizing anti-FeLV antibodies (J. Tartaglia et al., 1993, J. Virol. 67, p. 2370–2375). Newborn kittens are especially susceptive to FeLV infection. Since they do not have a matured immune system in the first weeks after birth, newborn kittens have to rely on the maternally derived antibodies for protection against FeLV infection. If vaccination did not provide the mother with neutralizing antibodies, the kittens will not be protected against FeLV and they will succumb to the infection.

Surprisingly it was found that a live recombinant leporipox virus comprising exogenous DNA encoding at least one antigen could be used to induce an antigenic or immunogenic response in a host which is normally not susceptible to productive infection of leporipox virus i.e. the leporipox virus is not able to replicate in said host after replication. Productive infection of leporipox viruses is restricted to lepori species only. Consequently infection of non-lepori species with a leporipox virus will not lead to replication of the leporipox virus. It was therefore surprising to find out that a live recombinant leporipox virus was capable of infecting a non-susceptible host and expressing said antigen in the absence of productive replication of the recombinant virus in said host, as evidenced by the fact that shedding of the virus vector to any other contact animal does not occur. More surprisingly, infection of a non-lepori host with said leporipox virus vector resulted in high expression levels of the antigen encoded by the exogenous DNA even though productive replication of the virus in said host was not observed. Growth of the viral vector in vitro does occur in some mammalian cell lines. Furthermore, due to the absence of productive replication of the leporipox virus vector in a such a non-susceptible host, the leporipox virus will be non-pathogenic in the non-lepori species, which makes these virus vectors even more suitable for vaccination.

Vaccination with a recombinant myxoma virus comprising exogenous DNA have been described in FR-A-2736358. The recombinant myxoma virus was used to vaccinate rabbits against myxomatosis and infectious diseases caused by other rabbit pathogens. Nowhere does FR-A-2736358 suggest the use of a live, recombinant myxoma virus as viral vector to induce an antigenic or immunogenic response in non-susceptible species, more particular non-lepori species.

Hence the present invention pertains to the use of a live, recombinant leporipox virus comprising exogenous DNA, which is operably linked to at least one expression control element and which is incorporated in a non-essential region of the virus genome, in the manufacture of a vector vaccine for the treatment and/or prophylaxis of infectious diseases in non-lepori species. Preferably a live, recombinant myxoma virus comprising exogenous DNA, which is operably linked to at least one expression control element and which is incorporated in a non-essential region of the virus genome, is used in the manufacture of a vector vaccine for the treatment and/or prophylaxis of infectious diseases in non-lepori species. More specifically the invention concerns the use of said live, recombinant leporipox virus in the manufacture of a vector vaccine for the treatment and/or prophylaxis of infectious diseases in avian-, feline-, canine-, porcine-, ovine-, bovine-, equine-, and human species. Preferably the live recombinant leporipox virus according to the invention is used to manufacture a vector vaccine for the treatment of infectious diseases in canine- and feline species.

The invention furthermore provides for a live recombinant leporipox virus comprising exogenous DNA operably linked to at least one expression control element, said exogenous DNA encoding at least one antigen of a pathogen that produces an infectious disease in non-leporidae. More specifically the exogenous DNA preferably encodes at least an antigen of a pathogen that causes an infectious disease in human-, bovine-, avian-, feline-, canine-, porcine-, equine- or ovine species. Preferably the exogenous DNA encodes an antigen of a feline- or canine pathogen. According to the invention the pathogen can be of viral-, bacterial or parasitic origin, depending on the disease against which the subject has to be vaccinated. If the pathogen has an RNA genome, the antigen of interest may be encoded by cDNA corresponding to the gene. The exogenous DNA may encode two or more antigens, which can be derived from the same pathogen or from different pathogens.

Suitable exogenous DNA for use in a recombinant leporipox virus preferably encodes viral glycoproteins, viral envelope proteins, viral matrix proteins, bacterial outer membrane proteins, bacterial enterotoxins, bacterial fimbriae or parasitic proteins. The exogenous DNA more specifically encodes the Feline Leukaemia virus (FeLV) envelope protein (Stewart et al. (1986) J. Virol. 58 pp. 825–834) or matrix protein (Donahue et al., 1988, J. Virol. 62, p. 722–731), feline- or sheep chlamidia major outer membrane protein (GenBank Accession No.'s CPFPNMOMP and CHTMOMPX, respectively), feline panleukopenia virus (FPV) VP2 protein (Carlson, J. et al., 1985, J. Virol. 55, p. 574–582), feline calicivirus capsid protein (M. J. Carter et al. 1992, J. Arch. Virol. 122, p. 223–235), feline immunodeficiency virus (FIV) Gag, Pol, Rev, Tat or Vif proteins (R. I. Talbot et al. 1989, Proc. Natl. Acad. Sci. USA 86, p. 5743–5747; T. R. Philips et al. 1990, J. Virol. 64, p. 4605–4613; K. M Lockridge, et al. 1999, J. Virol. 261, p. 25–30), feline infectious peritonitis virus (FIPV) membrane-nucleocapsid- or or spike protein (R. J. de Groot et al. 1987, J. Gen. Virol. 68, p. 2639–2646; H. Vennema, et al. 1991, Virology, 181, p. 327–335), canine distemper virus Env, HA, fusion- or nucleocapsid protein (M. Sidhu, et al. 1993, Virology 193, p. 66–72; U. Gassen, et al. 2000, J. Virol. 74, p. 10737–10744), canine parvovirus VP2 protein (Reed, P. et al., 1988, J. Virol. 62, p. 266–276), rabies virus glycoprotein G (T. J. Wiktor, et al. 1984, Proc. Natl. Acad. Sci. USA 81, p. 7194–7198), canine corona virus spike protein (B. Horsburgh, et al. 2000, J. Gen,. Virol. 73, p. 2849–2862). In addition to genes encoding immunogenic proteins from non-lepori pathogens, the exogenous DNA may also comprise genes encoding cytokines such as for example INFγ (GenBank Acc. No. D30619), IL-1β (GenBank Acc. No. M92060), IL-2/15 (GenBank Acc. No. AF054601), IL4, IL-5 (GenBank Acc. No. AF025436), IL-6, IL-12 (GenBank Acc. No. U83184 and U83185), IL-16 (GenBank Acc. No. AF003701) or IL-18 (GenBank Acc. No. ABO46211), or chemotactic cytokines such as the α-chemokines IL-8 (GenBank Acc. No. XM003501), GROα, GROβ, NAP-2, PF4, IP10, CTAP-III, β-TG and the β-chemokines MCP-1 (GenBank Acc. No. NM002982), MIP-1α, MIP-1β, RANTES (GenBank Acc. No. XM012656), MCP-2 (GenBank Acc. No. AJ251190), MCP-3 (GenBank Acc. No. NM 006273), MCP-4 (GenBank Acc. No. AJ251191). Preferably the genes encoding suitable cytokines according to the invention are derived from the same species the vaccine will be administered to.

The exogenous DNA is operably linked to at least one expression control element, which will control and regulate the expression of said exogenous DNA. In a preferred embodiment each gene present in the exogenous DNA is controlled by a separate and distinct expression control element. Expression control elements are known in the art and include promoters. Suitable promoters for expression of the exogenous DNA according to the invention are viral or synthetic promoters, which are able to modulate expression in the cytoplasm. Promoters useful in the present invention are poxvirus promoters, preferably a vaccinia promoter (see DE-A19627193; Mackett et al., "DNA Cloning Volume III", ed. D. M. Glover, 1985, IRL Press Ltd.). Preferred promoters according to the invention are synthetic promoters, more preferably synthetic early- or early/late promoters. Synthetic vaccinia virus early/late promoters are described in Chakrabati et al., BioTechniques 23, vol. 6, pp. 1094–1097, 1997.

The promoters can be synthesized by using standard techniques in the art, such as for example described in Chakrabafi et al., 1997 supra.

Suitable leporipox viruses that can be used according to the invention include but are not limited to myxoma viruses or Shope Fibroma viruses. Suitable myxoma virus strains include Lausanne strain (from ATCC), SG33 (Mainil, M. D. et al. 2000, J. Comp. Pathol. 122, p. 115–122). Borghi and Boerlage (Fenner & Fantini, "Biological control of Vertebrate Pests", CABI publishing 1999, ISBN 0 85199 323 0 and references therein). Suitable Shope Fibroma Virus strains include Original A strain (ATCC cat. No. VR-112) and Kasza strain (ATCC cat. No. VR-364). Preferably the live recombinant leporipox virus according to the invention is derived from a rhyxoma virus. Due to its host-restriction to lepori species, the leporipox virus is not virulent in a non-lepori host. It is however preferred to use an attenuated leporipox virus to generate the live recombinant viruses of the invention. For the purpose of the invention an attenuated leporipox virus is defined as a leporipox virus that is capable of productive replication in its target lepori host without causing disease. Attenuation of Leporipox virus strains can be carried out by serial passage of the strain or by deletion of one or more virulent genes that are not essential for viral replication. The complete DNA sequence of leporipox virus genome, its genomic organization and the localization of all open reading frames (ORF's) is presented in Cameron et al., Virology 264, p. 298–318 (1999). The complete DNA sequence of Shope Fibroma virus genome, its genomic organization and the localization of all open reading frames (ORF's) is presented in Willer et al., Virology 264, p. 319–343, (1999).

The exogenous DNA according to the invention is preferably inserted in a non-essential gene region of the leporipox virus genome. More preferably the exogenous DNA is inserted in a non-essential gene region that is involved in the virulence of the leporipox virus. Suitable non-essential gene regions of the myxoma virus genome or Shope Fibroma virus genome are the TK gene encoding Thymidine kinase, the M11L ORF, SERP-1, -2 and -3 ORF's and MGF ORF (Cameron et al, 1999, supra; Willer et al, 1999 supra). In a preferred embodiment of the invention one or more of the non-essential viral genes are deleted followed by insertion of the exogenous DNA and promoter. Deletion of at least part of the MGF ORF is especially preferred since this ORF encodes a virulence factor and is not essential for growth in vitro or in vivo (Graham et al., Virology 191, pp. 112–124, 1992). Deletion of the MGF ORF results in a decreased virulence of the leporipox virus.

The live recombinant leporipox virus according to the present invention can be produced using the in vivo recombination technique that involves insertion by site specific recombination of exogenous DNA into the leporipox virus genome. This can be accomplished using a method similar to the methods described for production of recombinant vaccinia virus and recombinant fowl pox virus (see U.S. Pat. No. 4,603,112; U.S. Pat. No. 5,093,258; Guo, P. X.; J. Virol. 63: 4189–4198 (1990); Mackett et al., "Construction And Characterization Of Vaccinia Virus Recombinants Expressing Exogenous Genes" in "DNA Cloning Volume III" ed. D. M. Glover, 1985, IRL Press Ltd.). In general, the live, recombinant leporipox virus according to the present invention can be produced using site-specific recombination between a parental leporipox genome and a DNA vector carrying the exogenous DNA under control of at least one expression control element. Suitable DNA vectors for use in site-specific recombination can be derived from any plasmid that comprises a multiple cloning site. The DNA vector comprises the exogenous DNA linked to at least one expression control element and located between viral DNA sequences homologous to a region of the leporipox genome into which the exogenous DNA is to be incorporated. The viral DNA sequences flanking the exogenous DNA are preferably selected from a region that is nonessential for replication of the leporipox virus. The DNA vector for recombination with the leporipox genome may additionally comprise a gene that codes for a selection marker under control of a pox virus promoter. The additional gene and promoter are also located between the viral DNA sequences derived from the leporipox genome. The DNA vector is transfected into host cells infected with a parental leporipox virus. Suitable host cells are eukaryotic cells which are permissive for the leporipox virus and which are transfectable by the DNA vector. Examples of host cells are rabbit kidney cells LLC-RK1 and RK13, rabbit lung cells R9ab, rabbit skin cells SF 1 Ep, DRS and RAB-9, rabbit cornea cells SIRC, rabbit carcinoma cells Oc4T/cc, rabbit skin/carcinoma cells CTPS, Vero cells, all available from ATCC.

Parental leporipox virus suitable for generating the live, recombinant leporipox viruses of the present invention are myxoma virus strains such as Lausanne strain (from ATCC), SG33 (Mainil, M. D. et al, 2000, J. Comp. Pathol. 122, p. 115–122), Borghi and Boerlage (Fenner & Fantini, "Biological control of Vertebrate Pests", CABI publishing 1999, ISBN 0 85199 323 0 and references therein), and Shope Fibroma Virus strains including Original A strain (ATCC cat. No. VR-112) and Kasza strain (ATCC cat. No. VR-364). Preferably myxoma virus strains are used to produce the live recombinant lepori virus according to the invention. Preferably the parental leporipox virus is an attenuated virus i.e. a leporipox virus that is able to productively replicate in its target lepori host without causing disease. Attenuation of Leporipox virus strains can be carried out by serial passage of the strain or by deletion of one or more virulent genes that are not essential for viral replication (for complete genomic sequence and localisation of genes see Cameron et al. 1999, supra and Willer et al. 1999, supra).

The virus is allowed to replicate in the host cell during which recombination occur between the leporipox DNA sequences on the DNA vector and the corresponding DNA on the parental leporipox genome. The recombination results in the insertion of the exogenous DNA linked to the expression control element(s) into the leporipox genome. The recombinant leporipox viruses are selected and purified using standard selection or screening methods well known in the art including detection of the integrated exogenous DNA by hybridization with probes homologous to the exogenous DNA, detection of expression of the selection marker co-integrated with the exogenous DNA, and detection of absence of the expression product of the deleted leporipox gene into which the exogenous DNA has been incorporated. Insertion of the exogenous DNA in the recombinant leporipox viral genome can be confirmed by polymerase chain reaction analysis.

The recombinant leporipox virus vector according to the invention is especially suitable for use as immunizing agent in non-leporidae because expression levels of the antigen can be reached in vivo that are sufficient for immunization of the host. Due to its restricted host-range the virus is attenuated in a non-lepori host hence there is no risk of disease caused by the leporipox virus. The host-restriction will furthermore prevent the leporipox viruses according to the invention from spreading among hosts, which are not targeted for vaccination. Thus in a further embodiment the present invention provides for a pharmaceutical composition, more preferably a vaccine comprising a pharmaceutical acceptable carrier and a live recombinant leporipox virus comprising exogenous DNA operably linked to at least one expression control element and incorporated in a non-essential region of the virus genome, said exogenous DNA encoding at least one antigen of a pathogen that produces an infectious disease in non-leporidale. The vaccine according to the invention preferably comprises a pharmaceutical acceptable carrier and a live recombinant myxoma virus according to the present invention expressing at least an immunogenic protein of a non-lepori pathogen. A recombinant leporipox virus according to the invention expressing two or more immunogenic proteins is specifically suitable for the manufacture of a multivalent vaccine.

Vaccine compositions according to the invention can be prepared following standard procedures. The recombinant leporipox virus can be grown on a cell culture for which the virus is permissive such as rabbit kidney cells LLC-RK1 and RK13, rabbit lung cells R9ab, rabbit skin cells SF 1 Ep, DRS and RAB-9, rabbit cornea cells SIRC, rabbit carcinoma cells Oc4T/cc, rabbit skin/carcinoma cells CTPS, Vero cells, all available from ATCC. The viruses thus grown can be harvested by collecting the tissue cell culture fluids and/or cells. Optionally, during harvesting the yield of the viruses can be promoted by techniques that improve the liberation of the infective particles from the growth substrate, e.g. sonication and freeze thawing. The live vaccine may be prepared in the form of a suspension or may be lyophilized.

Pharmaceutical acceptable carriers that are suitable for use in a vaccine according to the invention are sterile water, saline, aqueous buffers such as PBS and the like. In addition the vaccine according to the invention may comprise other additives such as adjuvants, stabilizers, anti-oxidants and others.

Suitable stabilizers are for example carbohydrates including sorbitol, mannitol, starch, sucrose, dextran and glucose, proteins and degradation products thereof including but not limited to albumin and casein, protein-containing agents such as bovine serum or skimmed milk, and buffers including but not limited to alkali metal phosphates. In lyophilized vaccine compositions it is preferable to add one or more stabilizers.

Suitable adjuvants include but are not limited to aluminum hydroxyde, phosphate or oxide, amphigen, tocophenols, monophosphenyl lipid A, muramyl dipeptide, oil emulsions, glucans, carbomers, block copolymers, cytokines and saponins such as Quil A. The amount of adjuvant added depends on the nature of the adjuvant itself. Cytokines such as INFγ, IL-12, IL18 are very suitable for use in a vaccine according to the invention.

Preferably the recombinant leporipox viruses according to the invention are administered to the non-lepori species via parenteral administration routes including but not limited to intramusculair, intradermal, or subcutaneous routes. Alternatively, the vaccine can be administered via non-parenteral administration routes such as oral, spraying, intraocular, intranasal or in ovo administration.

In general the recombinant leporipox virus according to the invention is administered in an amount that is effective to induce adequate expression levels of the exogenous protein. The dose generally will depend on the route of administration, the time of administration, as well as age, health and diet of the animal to be vaccinated. The recombinant leporipox virus can be administered in an amount between $10^2$ and $10^{11}$ pfu/dose per subject, preferably between $10^4$ and $10^9$ pfu/dose and more preferably $10^6$ to $10^7$ pfu/dose per subject (pfu is "plague forming units").

The vaccines according to the invention also may be given simultaneously or concomitantly with other live or inactivated vaccines. These additional vaccines can be administered non-parenteral or parenteral. Preferably the additional vaccines are recommended for parenteral administration.

The following experiments are illustrative for the invention and do not limit the invention to the particular embodiments described.

LEGENDS TO THE FIGURES

FIG. 1: schematic representation of construction of intermediate plasmids $pV_L$ and $PV_{EL}$. RHD represents cDNA of rabbit haemorrhagic virus. ab(5') and cd(3') represent the myxoma virus MGF flanking regions. Promoter represents synthetic late or early/late promoter, respectively. "mcs" represents nucleotide sequence comprising multiple cloning sites for introduction of exogenous DNA.

FIG. 2: the various recombinant DNA plasmids based on $pV_L$ $pV_{EL}$ which have been constructed. P represents the synthetic late ($pV_L$) or early/late ($pV_{EL}$) promoter region; ab(5') and cd(3') represent the myxoma virus MGF flanking regions. RHDV Vp60 represent the gene encoding RHDV VP60 protein. FeLV gp85 represents the Feline Leukaemia-virus env gene. FCV Vp60 represents gene encoding feline calicivirus capsid protein. FPL Vp2 represents feline panleukopenia virus vp2 gene. CPV VP2 represents canine parvovirus vp2 gene. GFP represent gene encoding green fluorescent protein. All plasmids comprise $Amp_r$ as selection marker (not shown).

EXAMPLES

Example 1

Preparation of Intermediate DNA Plasmids $pV_L$ and $pV_{EL}$

The starting plasmid for the procedure was the commercially available plasmid pCITE 2-b (Novagen inc.) containing a cDNA of rabbit haemorrhagic disease virus (Meyers G., et al. 1991, Virology 184, p. 664–676) inserted into the SalI and HincII sites of the vector. This plasmid is referred to as pCITE/RHD The first step was the introduction of the MGF flanking sequences. PCR primers myx a and myx b were used to amplify the 5' flanking sequence.

```
myx a: 5' TTCTCGGAAGTCATAGACGGTATT 3'           (seq id no 1)

myx b: 5' CATGCCAATGGCACATAAGAGAGTTGCGACTAGGTC 3' (seq id no 2)
```

A 2 μl sample of tissue culture grown MR24 ($10^6$ pfu ml$^{-1}$) was used as template for the PCR reaction, which was carried out using PCR Beads (Pharmacia) following the manufactures instructions. The PCR fragment was cloned using standard laboratory methods as a NcoI/blunt fragment into pCITE/RHD. The pCITE/RHD was first prepared by digestion with KpnI, followed by "blunting" with T4 DNA polymerase, then digestion with NcoI. The resulting plasmid was called pCITE/RHDab.

A second PCR reaction on an identical template preparation using the primers

```
myx c: 5' CGGCTCGAGCTAATTACCATTAAGTAACCCGTTTTACA 3' (seq id no 3)
             XhoI myx d: 5' GCTCTAGATATATCGTGTACGTAGTTCCCAAAAC 3'       (seq id no 4)
            XbaI
``` was performed to prepare the 3' flanking sequence. The PCR fragment was cloned as a XhoI/XbaI fragment into XhoI/XbaI cut pCITE/RHDab. The resulting plasmid was called pCITE/RHDabcd.

Synthetic pox virus promoters were then produced by the hybridization of the following oligonucleotides:

```
Vp3: 5' CTTTTTTTTTTTTTTTTTTTAGATCTTAAATGCC 3'        (seq id no 5)

Vp4: 5' CATGGGCATTTAAGATCTAAAAAAAAAAAAAAAAAAAGGTA 3' (seq id no 6)
```

These two complementary oligonucleotides anneal together to give cohesive ends compatible with KpnI and NcoI restriction sites. Likewise the following two oligonucleotides also anneal together give a KpnI/NcoI compatible fragment.

```
Vp5: 5' CAAAAATTGAAATTTTATTTTTTTTTTTGGAATATAAATAC 3'         (seq id no 7)

Vp6: 5' CATGGTATTTATATTCCAAAAAAAAAAAATAAAATTTCAATTTTTGGTAC 3'  (seq id no 8)
```

Vp5 and Vp6 together constitute an early/late promoter, whereas Vp3 and Vp4 produce a late promoter (Chakrabarti et al. Biotechniques 23, p. 1094–1097, 1997). One or other of the annealed oligonucleotide pairs was then cloned into KpnI/NcoI cut pCITE/RHDabcd, to produce pVP/RHD (late promoter) or pEL/RHD (early late promoter). Because the RHD capsid gene is not in frame with the first methionine in either of the two constructs (pVP/RHD and pEL/RHD) it was necessary to re-clone the RHD capsid gene(Vp60) and remove the intervening sequence in order to obtain expression. The plasmids pVP/RHD and pEL/RHD were cut with NcoI and EcoRI to remove the Vp60 coding sequence and the non coding sequence 5' to the initiating ATG. The Vp60 gene was then replaced by a PCR generated fragment produced using the following oligonucleotides:

```
5' GCTCCATGGAGGGCAAAGCCCGTG 3'      (seq id no 9)
      NcoI

5' TTGCTCAGGACACCGGCACCTGC 3'       (seq id no 10)
```

Template for the PCR reaction was pCITE/RHD. The PCR generated fragment was digested with NcoI and EcoRI and cloned into the prepared pVP/RHD and pEL/RHD. The resultant plasmids were termed pVP/Vp60 and pEL/Vp60. In order to allow for the introduction of genes flanked by other restriction sites a multiple cloning site was introduced downstream of the unique NcoI site in pVP/Vp60 and pEL/Vp60. The following oligonucleotides:

```
mcs A: 5'CATGGATCGATGTCGACGGATCCACTAGTGAATTCACGCGTC 3'  (seq id no 11)

mcs B: 5'TCGAGACGCGTGAATTCACTAGTGGATCCGTCGACATCGATC 3'  (seq id no 12)
``` anneal to give overhanging ends compatible with NcoI and XhoI restriction endonuclease sites. Replacement of the NcoI/XhoI fragment, which carries all of the RHD associated sequence, with the annealed oligonucleoudes results in the following two plasmids: $pV_L$ and $pV_{EL}$ (see FIG. 1).

The plasmids $pV_L$ and $pV_{EL}$ were used to construct various recombinant DNA plasmids comprising the follwing genes: rabbit haemorrhagic disease capsid protein VP60 (Meyers et al. 1991, supra), green fluorescent protein (Clonetech Laboratories Inc, Palo Alto, Calif., USA), feline leukaemia envelope glycoprotein gp85 (Stewart et al., 1986, J. Virol. 58, p. 825–834), feline leukaemia matrix (gag) proteins (Donahue et al., 1988, J. Virol. 62, p. 722–731), feline calicivirus capsid protein (GenBank Accession No's Z11536 and NC 001481), feline panleukopenia virus capsid protein VP2 (Carlson J. et al. 1985, J. Virol. 55, p. 574–582), canine parvovirus capsid protein VP2 (Reed P. et al, 1988, J. Virol. 62, p. 266–276). Table 1 lists the various DNA plasmids that were constructed to produce the recombinant myxoma viruses according to the invention. Each recombinant plasmid was constructed in the same way, in that the target gene was either cut from an existing plasmid or amplified by PCR such that restriction enzyme sites at the ends of the gene were compatible with sites in the mCs of $pV_L$ or $pV_{EL}$.

Preparation of DNA Plasmid $pV_L$GFP

A plasmid containing GFP gene was purchased from Clonetech laboratories, Inc, Palo Alto, Calif., USA and digested with NcoI and EcoRI to cut the GFP gene from the plasmid. The gene was inserted in $pV_L$ resulting in $pV_L$GFP.

Preparation of DNA Plasmid $pV_{EL}FeLV_{enV}$

The envelope gene was amplified by PCR from pFGA5 (Stewart et al 1986 supra) using the oligonucleotides:

```
                                           (seq id no 13)
5' CAC ATCGAT TGA TGG AAA GTC CAA CGC 3'
       ClaI (seq id no 14)
5' TGGAATTCA TGG TCG GTC CGG ATC GTA 3'
     EcoRI
```

The PCR fragment was digested with ClaI and EcoRI and inserted into $pV_{EL}$ resulting in $pV_{EL}FeLV_{env}$.

Preparation of DNA Plasmid $pV_{EL}$FPL

The FPL capsid gene was obtained by PCR amplification from replicative form (rf) DNA by PCR using the following primers:

```
5' CACATCGATTGATGAGTGATGGAGCAG 3'  (seq id no 15)

5' CGGGAATTCTAGGTGCTAGTTGATATG 3'  (seq id no 16)
```

The rf DNA was prepared from feline kidney cells (CRFK) infected with a vaccine strain of FPL by standard methods (Reed, P. et al. 1988, J. Virol. 62, p. 266–276)

Preparation of DNA Plasmid $pV_{EL}$FCV

Feline kidney cells (CRFK) were infected with FCV strain F9 at a multiplicity of 0.1 pfu per cell. After thirty six hours the cells were harvested and total RNA was prepared using Guanidine isothiocyanate (TRIzol reagent GibCoBRL). First strand cDNA synthesis was carried out using oligodt primers (SuperScript Choice GibCo BRL). The complete nucleotide sequence and genomic organisation of the F9 strain of FCV has been reported (GenBank Accession Number M86379). Oligonucleotides were synthesised to prime second strand DNA synthesis and to subsequently PCR amplify the capsid gene. The following oligonucleotides were used to produce the Vp60 capsid protein gene of FCV (F9 strain):

```
5' GGATCGATGCGCGGATGACGGGTCAATC 3'   (seq id no 17)
     ClaI

5' GGGGACTAGTATTCATAACTTAGTCATGGG 3' (seq id no 18)
       SpeI
```

The Vp6ocapsid gene was inserted into the mcs of $pV_L$ and $pV_{EL}$ resulting in $pV_L$FCV and $pV_{EL}$FCV respectively.

Preparation of DNA Plasmid $pV_{EL}$CPV

The gene encoding capsid protein VP2 was PCR amplified from CPV vaccine strain of Nobivac Parvo®, digested with NcoI and EcoRI and inserted in $pV_{EL}$.

Example 2

Preparation of Recombinant Myxoma Virus

A non-pathogenic strain of myxoma virus (designated MR24), which had been attenuated by prolonged passage in rabbit kidney cells (RK13) was selected. This attenuated myxoma virus (MR24) was shown to be non-pathogenic (0% mortality) in rabbits when administered to rabbits by the subcutaneous, intra-dermal or intramusculair routes. MR24 is a candidate myxomatosis vaccine strain for use in rabbits. All viral titrations and amplifications were carried out in rabbit kidney (RK-13) cells.

Recombinant myxoma viruses were produced following the methods described for constructing recombinant vaccinia viruses (Mackett et. al. 1985, supra). To do this rabbit kidney cells (RK13) were infected with myxoma virus MR24 at a multiplicity of 0.1 pfu per cell. After two hours the cells were then transfected with plasmid DNA using the lipofectamine transfection reagent (GibCo BRL). Selection for recombinant viruses was based on limiting dilution and identification by immunofluorescence.

Seventy two hours post transfection the infected/transfected cell cultures were freeze thawed three times in order to release virus. This primary mix of wild type and recombinant virus was diluted 50 fold with tissue culture medium and then 10 microlitres of the virus mix was used to infect each well of a 96 well tissue culture plate previously seeded with RK13 cells. The 96 well plate was then incubated for 72 hours to allow infection and propagation of the virus to proceed. After this time the plate was treated to three cycles of freezing and thawing whilst maintaining the individual status of each well of the plate. This became the first round master plate. Subsequently 5 microlitres of virus containing medium from each well was plated onto a duplicate 96 well plate seeded with RK13 cells. After 48 hours the duplicate plate was fixed with ice cold methanol and the plate screened for expression of the recombinant protein by immunofluorescence.

For example, the cells infected and transfected with $pV_{EL}FeLV_{env}$ were screened for the production of FeLV envelope protein as follows; mouse monoclonal antibody 3–17 (European Veterinary Laboratory, Woerden The Netherlands) ascitic fluid was diluted 1000 fold then added to each well of the fixed 96 well plate. The plate was incubated at 37° C. for one hour. The plate was subsequently washed 5 times with PBS and then incubated with FITC labeled rabbit anti mouse IgG (Sigma Chemical Co), incubation was then continued for another hour. Finally the plate was washed 5 times with PBS and examined under a fluorescence microscope. Wells containing fluorescent foci of infection were identified and noted. The corresponding wells from the first round master plate were then diluted over more RK-13 seeded 96 well plates, which in turn became second round master plates. The process of gradual enrichment was continued until recombinant viruses constituted 20–50% of the total virus. Expression of the recombinant protein of the other recombinant myxoma viruses was screened in a similar way.

TABLE 1

DNA plasmids and the corresponding recombinant myxoma viruses.

| Plasmid | Recombinant Virus | Strain number |
|---|---|---|
| $pV_L$/GFP | Myxo/GFP | Not assigned |
| $pV_L$/VP60 | Myxo/RHD | Not assigned |
| $pV_{EL}$/FeLV$_{env}$ | Myxo/FeLV$_{env}$ | MS0011 |
| $PV_{EL}$/FCV | Myxo/FCV | MS0013 |
| $PV_L$/FCV | Myxo/FCV | MS0014 |
| $PV_{EL}$/FPL | Myxo/FPL | MS0015 |
| $PV_{EL}$/CPV | Myxo/CPV | MS0016 |

Final purification of the recombinants was achieved by picking individual foci of infection from agar overlaid cultures.

Example 3

Myxo/RHD in Chickens

To determine whether non-lepori species infected with the recombinant myxoma viruses would elicit an antibody response, chickens were immunized with myxo/RHD by the subcutaneous or intramuscular route. The birds received $10^5$ pfu of virus on day 0 and day 14 of the immunization schedule. Blood samples were taken at days, 0, 14 and 28 and analyzed for antibodies to RHDV, the results are shown in table 2. All the birds remained clinically normal throughout the experiment.

TABLE 2

Results of inoculation of chickens with myxo/RHD.
Antibody levels are expressed as a reciprocal of
that dilution of sera which inhibits the agglutination of
rabbit red blood cells by 4 units of purified RHDV antigen

| Route of Inoculation | Animal Number | Haemagglutination Inhibition titre | | |
|---|---|---|---|---|
| | | Day 0 | Day 14 | Day 28 |
| Intra-muscular | 166 | 0 | 80 | 40 |
| | 168 | 0 | 40 | 20 |
| | 170 | 0 | 640–1280 | 640–1280 |
| | 172 | 0 | 40 | 40 |
| | 174 | 0 | 320 | 320 |
| | 176 | 0 | 40 | 160 |
| | 178 | 0 | 320 | 640 |
| | 180 | 0 | 40 | 40 |
| sub-cutaneous | 182 | 0 | 320 | 320 |
| | 184 | 0 | 40 | 20 |
| | 186 | 0 | 10 | 10 |
| | 189 | 0 | 320–640 | 320 |
| | 191 | 0 | 40 | 40 |
| | 193 | 0 | 20 | 20 |
| | 195 | 0 | 640 | 640 |
| | 197 | 0 | 320 | 320 |

TABLE 2-continued

Results of inoculation of chickens with myxo/RHD.
Antibody levels are expressed as a reciprocal of
that dilution of sera which inhibits the agglutination of
rabbit red blood cells by 4 units of purified RHDV antigen

| Route of Inoculation | Animal Number | Haemagglutination Inhibition titre | | |
|---|---|---|---|---|
| | | Day 0 | Day 14 | Day 28 |
| Controls | 290 | 0 | 0 | 0 |
| | 292 | 0 | 0 | 0 |
| | 294 | 0 | 0 | 0 |
| | 296 | 0 | 0 | 0 |
| | 298 | 0 | 0 | 0 |

Example 4

Myxo FCV in Cats

An experiment was set up to establish the efficacy of a myxoma/feline calicivirus capsid recombinant virus (myxo/FCV) to induce a neutralising antibody response and protect cats from challenge with virulent feline calicivirus. A group of 4 cats (Group 1) were immunised subcutaneously with $5\times10^6$ focus forming units (ffu) of myxo/FCV. The immunisation was repeated at 3 weeks post first immunisation. Four unvaccinated control animals (Group 2) were housed with the test animals. Four weeks after the second immunisation all the cats were challenged intranasally with $10^{5.3}$ $TCID_{50}$ of a virulent strain of feline calicivirus. The challenge virus was introduced dropwise, 0.5 ml into each nostril.

TABLE 3

Schedule of Procedures

| Time points | ANIMAL GROUPS | PROCEDURE |
|---|---|---|
| Day - 1 | 1&2 | Swab O/P, nasal.<br>Bleed |
| Day 0 | 1 | Vaccinate |
| Day 21 | 1 | Bleed and 2nd vaccination |
| Day 49 | 1&2 | Bleed and Challenge |
| Days 50–62 | 1&2 | Clinical monitoring<br>Swab O/P, nasal |
| Day 63 | 1&2 | Clinical monitoring<br>Bleed<br>Swab O/P, nasal |

Swabs were taken at the start of the experiment to ensure that none of the animals had feline calicivirus present in the oro-pharynx. Similarly blood samples were taken to ensure that none of the animals had anti-FCV antibodies prior to the commencement of the study. Swabs were taken after challenge to examine excretion of virus.

Blood samples taken during the experiment were used in virus neutralization assays. These assays determine the levels of circulating antibodies in the cat. It is well known that the serum neutralizing antibodies are present in convalescent animals, and that pre-existent neutralizing antibodies provided as a result of vaccination help in providing protection from disease (Hohdatsu, et. al. 1999 J. Vet. Med. Sci. 61, 299–301).

TABLE 4

Results of inoculation (serum neutralization titre) of cats with myxo/FCV (MS0013). The figures show the maximum serum dilution at which virus neutralisation is obtained. The blood samples taken prior to vaccination (Prebleed) show no antibodies to FCV. Serum diluted 1–4 fold will show a non-specific inhibition of viral growth in vitro.

| SERUM | | Pre- | POST 1ST | POST 2ND | Post | Clinical |
|---|---|---|---|---|---|---|
| Cat No | Group | bleed | VAC. | VAC | Challenge | Score* |
| 358–054 | Vaccinates | <1:4 | 1:102 | 1:2580 | 10321 | 1 |
| 376–561 | (Group 1) | <1:4 | 1:50 | 1:1024 | >16384 | 13 |
| 383–882 | | <1:4 | 1:215 | 1:3444 | 13777 | 0 |
| 073–609 | | <1:4 | 1:161 | 1:1569 | 16384 | 4 |
| 295–099 | Controls | <1:4 | <1:4 | <1:5 | 1337 | 49 |
| 375–369 | (Group 2) | <1:4 | <1:4 | <1:4 | 4096 | 18 |
| 078–001 | | <1:4 | <1:4 | <1:4 | 2435 | 47 |
| 268–054 | | <1:4 | <1:4 | <1:4 | 697 | 22 |

*The clinical scoring scheme used is that set out in the European Pharmacopoeia for the production of a Feline Calicivirus vaccine (Third edition June 1996 ISBN 92-871-2991-6) this states that the vaccine complies with the test if the clinical score is significantly lower than that of the controls. In this study the vaccinated group has a mean clinical score of 4.5 compared with 34 for the controls.

Comparing the results obtained after vaccination with myxo-FCV (Table 4) with those of conventional vaccines (Table 5), it is clear that after the first vaccination the Group 1 animals have an antibody response comparable to animals given two doses of many commercial vaccine. Indicating that these cats would be protected from disease. After the second vaccination the antibody titres are well in excess of those obtained by commercial vaccines preparations (Hohdatsu, et. al. 1999 J. Vet. Med. Sci. 61, 299–301, DeSilver et. al. 1997, Proc. 1st Int. Symp. Calicivirus ESVV 131–143).

TABLE 5

Neutralising antibody titres of commercially available FCV vaccine immune sera against FCV strains*

| FCV | Immune serum | | | | | | | |
|---|---|---|---|---|---|---|---|---|
| | Vaccine A | | Vaccine B | | Vaccine C | | Vaccine D | |
| isolate | #20[a)] | #C3 | #C1 | #C4 | #C2 | #C5 | #C6 | #A7 |
| F4 | 20[b)] | 80 | 10 | 5 | 5 | 5 | 160 | 20 |
| F9 | 160 | 160 | 640 | 40 | 10 | 10 | 160 | 320 |
| 255 | 10 | 20 | 20 | 5 | <5 | <5 | 640 | >640 |
| 91-1 | <5 | <5 | <5 | <5 | <5 | <5 | 5 | <5 |

[a)]Serum Number
[b)]Neutralization titre
*Taken from Hohdatsu, et. al. (1998)

Feline herpes virus vectors expressing FCV antigens also induce very low titres of serum neutralising antibodies (in the region 2.5 and 3.0) prior to challenge as reported by Yokoyama et. al. (1998).

References

Hohdatsu T, Sato K, Tajima T & Koyama H. Neutralizing feature of a commercially available feline calicivirus (FCV) vaccine immune sera against FCV field isolates. J Vet Med Sci 1999; 61:299–301.

Yokoyama N. Fujita K, Damiani et al. Further development of a recombinant feline herepesvirus type 1 vector expressing feline calicivirus immunogenic antigen. J of Vet Med Sci 1998; 60:717–723.

Reed L J & Meunch H. A simple method of estimating fifty per cent end points. Am J of Hygiene 1938; 27:493–497.

Example 5

Netralization Experiments with Myxo/FCV in Pigs and Bovines

The applicability of the myxoma virus as an eukaryotic expression vector for the induction of a protective immune response in non-natural hosts i.e. bovine and pigs was tested by intra-dermal and intra-muscular route of injection.

A myxoma virus vector containing the feline calicivirus gene fragment encoding for the mature form of the capsid antigen was used both in calves as well as pigs. Two groups comprising four calves of 12 weeks old and four pigs of 6 weeks old were included in this study.

Blood samples (10 ml/animal) were collected one week before start of the study in order to test whether the animals were sero-negative to feline calicivirus.

Subsequently, all animals were injected both intra-dermally as well as intramuscularly with 1 ml PBS containing $1\times10^8$ FFU of the recombinant myxoma virus/route of injection/animal. The animals were housed as one group per species. After four weeks, blood samples (10 ml/animal) were collected and animals were re-injected intra-dermally and intramuscularly with the same dose of myxoma virus i.e. 1 ml of $1\times10^8$ FFU of the recombinant myxoma virus/route of injection/animal. Two weeks after the last injection, blood samples (10 ml/animal) were collected and animals were destroyed according to the guidelines for GMO testing in vivo. Collected blood samples were tested for the presence of antibodies directed against Calicivirus by means of a virus neutralisation assay in vitro.

TABLE 6

Experimental design and time frame: Groups consist either of four pigs or four calves.

| Date | Activity |
|---|---|
| T = −7 days | Pre-serum samples were collected |
| T = 0 days | Intra-dermal and intra-muscular injection with 1 ml PBS containing $1 \times 10^8$ FFU of myxoma virus per route of injection and per animal |
| T = 28 days p.i. | Blood samples were collected (10 ml) |
| T = 28 days p.i. | Intra-dermal and intra-muscular injection with 1 ml PBS containing $1 \times 10^8$ FFU of myxoma virus per route of injection and per animal |
| T = 42 days p.i. | Blood samples were collected |
| T = 42 days p.i. | Termination of experiment |

Method For FCV serum neutralisation assay

Serum neutralisation was assessed by c.p.e. on CrFK cells. Five fold replicates of two hundred $TCID_{50}$ of virus were mixed with serial dilutions, (commencing at 1:4), bf sera in a final volume of 600 microliter. Virus/sera mixtures were then incubated for 60 minutes at 37° C. in sterile 5 ml dilution tubes. 100 microliter of the test mixtures were then added 96 well tissue culture dishes seeded with CrFK cells in 100 microliter growth medium. Incubation was continued for 5 days. The $TCID_{50}$ values were calculated according to the method of Reed & Meunch [1].

Reed, L. J., and H. Meunch. 1938. A simple method of estimating fifty percent end points. Am. J. Hyg., 27:493–497.

TABLE 7

Results of Sns against FCV on Sera from Study FMD004

| Animal | Prebleed | Post 1st Vac | Post 2nd Vac |
|---|---|---|---|
| Bovine 2403 | <=1:4 | 1:54 | >=1:724 |
| Bovine 1948 | <=1:4 | 1:64 | >=1:1024 |
| Bovine 1603 | <=1:4 | 1:13 | 1:256 |
| Bovine1190 | <=1:4 | 1:54 | >=1:861 |
| Pig 122 | <=1:4 | <=1:4 | 1:304 |
| Pig 119 | <=1:4 | <=1:4 | 1:304 |
| Pig 118 | <=1:4 | 1:10 | 1:256 |
| Pig 117 | <=1:4 | <=1:4 | >=1:861 |

Example 6

Growth of Myxoma Virus Strains in Various Cell Types in Vitro

Cells were infected with recombinant myxoma viruses expressing green fluorescence protein constructed from 2 different strains of myxoma virus. Growth was assayed by an increase in the number of fluorescing cells over time Fluorescence was observed when the myxo/GFP recombinant virus was plated onto various cell types in culture, as shown in table 8. This indicated that the virus was able to enter and express the GFP gene in non rabbit cells. From Table 8 it shows that growth of the virus in vitro was observed in some cell types, and that the pattern differed for the two constructs tested.

TABLE 8 growth of myxoma vectors in various cell types in vitro.

| | Growth | |
|---|---|---|
| Cell Type | MS20-10 | MR24 |
| Rabbit Kidney (RK-13) | +++++ | +++++ |
| African monkey kidney (Vero) | +++++ | +++++ |
| Bovine embryo lung (BEL) | + | + |
| Feline embyo fibroblasts (FeF) | + | − |
| Chicken embryo fibroblasts (CEF) | + | − |
| Canine Tumor cell line A72 | − | − |

Example 8

ELISA For Responses to Canine Parvovirus Vaccination

In order to assess the immune responses elicited by vaccination of dogs with a recombinant myxoma virus expressing canine parvovirus capsid protein Vp2 an ELISA was setup. The responses to vaccination were compared with those found in conventionally vaccinated dogs Materials & Methods Mateials:

TBS (50 mM Tris buffered saline)

50 mM Tris-buffered Saline, pH 7.5

6.35 g Tris-HCl
1.18 g Tris Base
8.77 g NaCl
800 ml $dH_2O$
pH adjusted to 7.5 and volume brought to 1 L with $dH_2O$.
TBS-Tween
TBS was prepared as above then add 0.5 mL of TWEEN 20. Mix Well
Methods
1. Anti CPV monoclonal antibody was resuspended in 0.1 M $Na_2$ $CO_3$ buffer pH9.6 at a concentration of 5–10 microgram/ml. An ELISA plate was incubated overnight at 40C. with 100 microliter per well of the antibody suspension.
2. After shaking off excess antigen coating solution, remaining binding sites were blocked in each well by incubating with 200 microliter of 1% BSA and 2% dry milk powder in TBS at room temperature for one hour.
3. After shaking off the block solution, it was replaced with 100 microliter of tissue culture supernatant containing canine parvovirus at a titre of approx. $10^7$ p.f.u. $ml^{-1}$. Incubation was carried out at room temperature for 1–2 hours.
4. Plates were washed four times with TBS-Tween.
5. Serial dilutions of the serum to be tested were made in TBS. 100 microliter of these were added to the wells of the ELISA plate and incubation was continued for 1–2 hours at room temperature.
6. Afterwards the plate was washed four times in TBS-Tween.
7. An anti-dog alkaline phosphatase conjugated second antibody, (e.g ICN biomedical Research Products cat no. 675071) was added at a dilution indicated by the manufacturer. Incubation was carried out at room temperature for 1–2 hours
8. The plate was washed four times in TBS-Tween
9. The ELISA was developed by the addition of substrate PNPP (p-Nitrophenyl phosphate e.g SIGMA chemical company cat number N2770).
10. Absorbance was read in a spectrophotometer at 420 nm.

Results are presented in Table 9.

TABLE 9 results of ELISA for responses to CPV

| | Absorbance at indicated dilution | | | | | | | |
|---|---|---|---|---|---|---|---|---|
| Vaccine | 10 | 20 | 40 | 80 | 160 | 320 | 640 | 1280 |
| Myxo-Vp2 | >2.0 | >2.0 | 1.8 | 1.56 | 1.198 | 0.685 | 0.45 | 0.297 |
| Conventional | 0.73 | 0.46 | 0.29 | 0.30 | 0.28 | 0.30 | 0.26 | 0.29 |
| None | 0.31 | 0.28 | 0.30 | 0.26 | 0.28 | 0.25 | 0.27 | 0.26 |

The ELISA results clearly demonstrate that a dilution of 1:40 of the sera from conventionally vaccinated dogs results in a background level of aborbance i.e. that seen with unvaccinated dog sera. Whereas with myxoma-CPV(Vp2) vaccinated dog sera a dilution of 1:1280 is required to achieve the same background level.

We claim:

1. A method of treating a non-lepori species against contracting an infectious disease, comprising:

administering a live, recombinant leporipox virus comprising exogenous DNA, which is operably linked to at least one expression control element and which is incorporated in a non-essential region of the virus genome, wherein the exogenous DNA encodes at least one antigen that includes an antigenic or immunogenic response in the non-lepori species.

2. The method according to claim 1, wherein the non-lepori species is felines canines.

3. A composition, comprising:

a pharmaceutical acceptable carrier and a live, recombinant leporipox virus comprising exogenous DNA operably linked to at least one expression control element and incorporated in a non-essential region of the virus genome, said exogenous DNA encoding at least one antigen of a pathogen that produces an infectious disease in non-leporidae.

4. A live, recombinant leporipox virus, comprising:

exogenous DNA operably linked to at least one expression control element and incorporated in a non-essential region of the virus genome wherein said exogenous DNA encodes at least one antigen of a non-lepori pathogen.

5. A virus according to claim 4, wherein the leporipox virus is a myxoma virus.

6. The virus according to claim 4, wherein the exogenous DNA encodes at least an antigen of a feline or canine pathogen.

7. The virus according to claim 4, wherein the exogenous DNA encodes at least an antigen of a feline or canine virus.

8. The virus according to claim 4, wherein the exogenous DNA encodes a protein selected from the group consisting of Feline Leukaemia virus (FeLV) envelope protein, the Feline Calicivirus (FCV) capsid protein, the Feline Panleukopenia virus (FPL) VP2 protein, canine Parvovirus (CPV) VP2 protein and combinations thereof.

9. The virus according to claim 4, wherein the exogenous DNA and expression control element are inserted in the MGF ORF of the virus genome.

10. The virus according to claim 4, wherein the expression control element operably linked to the exogenous DNA is a synthetic poxvirus promoter.

11. The virus according to claim 10, wherein the promoter is an early/late promoter.

12. A pharmaceutical composition, comprising:

the live, recombinant leporipox virus according to claim 4, and a pharmaceutically acceptable carrier.

13. A vaccine, comprising:

a pharmaceutical acceptable carrier and a live, recombinant leporipox virus comprising exogenous DNA operably linked to at least one expression control element and incorporated in a non-essential region of the virus genome, said exogenous DNA encoding at least one protective antigen of a pathogen that produces an infectious disaese in non-leporidae.

* * * * *

SEQUENCE LISTING

```
<160> NUMBER OF SEQ ID NOS: 18

<210> SEQ ID NO 1
<211> LENGTH: 24
<212> TYPE: DNA
<213> ORGANISM: Artificial
<220> FEATURE:
<223> OTHER INFORMATION: PCR primer for 5' MGF flanking sequence

<400> SEQUENCE: 1
ttctcggaag tcatagacgg tatt                                    24

<210> SEQ ID NO 2
<211> LENGTH: 36
<212> TYPE: DNA
<213> ORGANISM: Artificial
<220> FEATURE:
<223> OTHER INFORMATION: PCR primer for 5' MGF flanking sequence

<400> SEQUENCE: 2
catgccaatg gcacataaga gagttgcgac taggtc                       36

<210> SEQ ID NO 3
<211> LENGTH: 38
<212> TYPE: DNA
<213> ORGANISM: Artificial
<220> FEATURE:
<223> OTHER INFORMATION: PCR primer for 3' MGF flanking sequence

<400> SEQUENCE: 3
cggctcgagc taattaccat taagtaaccc gttttaca                     38
```

```
<210> SEQ ID NO 4
<211> LENGTH: 34
<212> TYPE: DNA
<213> ORGANISM: Artificial
<220> FEATURE:
<223> OTHER INFORMATION: PCR primer for 3' MGF flanking sequence

<400> SEQUENCE: 4
gctctagata tatcgtgtac gtagttccca aaac                               34

<210> SEQ ID NO 5
<211> LENGTH: 35
<212> TYPE: DNA
<213> ORGANISM: Artificial
<220> FEATURE:
<223> OTHER INFORMATION: Synthetic pox virus promoter (late)

<400> SEQUENCE: 5
cttttttttt ttttttttttt tagatcttaa atgcc                             35

<210> SEQ ID NO 6
<211> LENGTH: 42
<212> TYPE: DNA
<213> ORGANISM: Artificial
<220> FEATURE:
<223> OTHER INFORMATION: Synthetic pox virus promoter (late)

<400> SEQUENCE: 6
catgggcatt taagatctaa aaaaaaaaaa aaaaaaaagg ta                       42

<210> SEQ ID NO 7
<211> LENGTH: 42
<212> TYPE: DNA
<213> ORGANISM: Artificial
<220> FEATURE:
<223> OTHER INFORMATION: Synthetic pox virus promoter (early/late)

<400> SEQUENCE: 7
caaaaattga aattttattt ttttttttg gaatataaat ac                       42

<210> SEQ ID NO 8
<211> LENGTH: 50
<212> TYPE: DNA
<213> ORGANISM: Artificial
<220> FEATURE:
<223> OTHER INFORMATION: Synthetic pox virus promoter (early/late)

<400> SEQUENCE: 8
catggtattt atattccaaa aaaaaaaat aaaatttcaa ttttttggtac              50

<210> SEQ ID NO 9
<211> LENGTH: 24
<212> TYPE: DNA
<213> ORGANISM: Artificial
<220> FEATURE:
<223> OTHER INFORMATION: PCR primer

<400> SEQUENCE: 9
gctccatgga gggcaaagcc cgtg                                          24

<210> SEQ ID NO 10
<211> LENGTH: 23
<212> TYPE: DNA
<213> ORGANISM: Artificial
<220> FEATURE:
<223> OTHER INFORMATION: PCR primer
```

<400> SEQUENCE: 10
ttgctcagga caccggcacc tgc                                    23

<210> SEQ ID NO 11
<211> LENGTH: 42
<212> TYPE: DNA
<213> ORGANISM: Artificial
<220> FEATURE:
<223> OTHER INFORMATION: PCR primer for multiple cloning site

<400> SEQUENCE: 11
catggatcga tgtcgacgga tccactagtg aattcacgcg tc               42

<210> SEQ ID NO 12
<211> LENGTH: 42
<212> TYPE: DNA
<213> ORGANISM: Artificial
<220> FEATURE:
<223> OTHER INFORMATION: PCR primer for multiple cloning site

<400> SEQUENCE: 12
tcgagacgcg tgaattcact agtggatccg tcgacatcga tc               42

<210> SEQ ID NO 13
<211> LENGTH: 27
<212> TYPE: DNA
<213> ORGANISM: Artificial
<220> FEATURE:
<223> OTHER INFORMATION: PCR primer for FeLV env

<400> SEQUENCE: 13
cacatcgatt gatggaaagt ccaacgc                                27

<210> SEQ ID NO 14
<211> LENGTH: 27
<212> TYPE: DNA
<213> ORGANISM: Artificial
<220> FEATURE:
<223> OTHER INFORMATION: PCR primer for FeLV env

<400> SEQUENCE: 14
tggaattcat ggtcggtccg gatcgta                                27

<210> SEQ ID NO 15
<211> LENGTH: 27
<212> TYPE: DNA
<213> ORGANISM: Artificial
<220> FEATURE:
<223> OTHER INFORMATION: PCR primer for FPL capsid gene

<400> SEQUENCE: 15
cacatcgatt gatgagtgat ggagcag                                27

<210> SEQ ID NO 16
<211> LENGTH: 27
<212> TYPE: DNA
<213> ORGANISM: Artificial
<220> FEATURE:
<223> OTHER INFORMATION: PCR primer for FPL capsid gene

<400> SEQUENCE: 16
cgggaattct aggtgctagt tgatatg                                27

<210> SEQ ID NO 17

-continued

```
<211> LENGTH: 28
<212> TYPE: DNA
<213> ORGANISM: Artificial
<220> FEATURE:
<223> OTHER INFORMATION: PCR primer for FCV VP60

<400> SEQUENCE: 17
ggatcgatgc gcggatgacg ggtcaatc                                    28

<210> SEQ ID NO 18
<211> LENGTH: 30
<212> TYPE: DNA
<213> ORGANISM: Artificial
<220> FEATURE:
<223> OTHER INFORMATION: PCR primer for FCV VP60

<400> SEQUENCE: 18
ggggactagt attcataact tagtcatggg                                  30
```